United States Patent [19]

Hyde et al.

[11] 4,330,865

[45] May 18, 1982

[54] NON-DESTRUCTIVE TEST APPARATUS

[75] Inventors: Eric A. Hyde; Hugh A. Goldsmith, both of Bristol; Michael J. Proudlove, Congleton, all of England

[73] Assignee: Nuclear Power Company Limited, London, England

[21] Appl. No.: 170,594

[22] Filed: Jul. 21, 1980

[30] Foreign Application Priority Data

Jul. 25, 1979 [GB] United Kingdom ................. 7925967

[51] Int. Cl.³ ............................................. G21C 17/00
[52] U.S. Cl. .................................. 376/249; 180/8 C; 180/901
[58] Field of Search ............... 376/249; 180/8 R, 8 C, 180/901; 114/222

[56] References Cited

U.S. PATENT DOCUMENTS

| | | | |
|---|---|---|---|
| 3,715,914 | 2/1973 | Gross et al. | 376/249 |
| 3,810,515 | 5/1974 | Ingro | 180/901 |
| 3,958,652 | 5/1976 | Urakami et al. | 180/901 |
| 3,987,666 | 10/1976 | Blanc et al. | 376/249 |
| 3,988,922 | 11/1976 | Clark et al. | 376/249 |
| 4,095,378 | 6/1978 | Urakami | 114/222 |

Primary Examiner—Sal Cangialosi
Attorney, Agent, or Firm—William R. Hinds

[57] ABSTRACT

A remotely controlled vehicle capable of roving over the outer surface of a nuclear reactor primary vessel carrying inspection instrumentation. The vehicle comprises an elongate bridge having a pair of suction support pads. Each pad carries gas thrusters for acting in opposition to the suction effort thereby to reduce adherence of the pads and enable displacement of the vehicle over the surface. The vehicle is supported by a services conducting umbilical.

8 Claims, 9 Drawing Figures

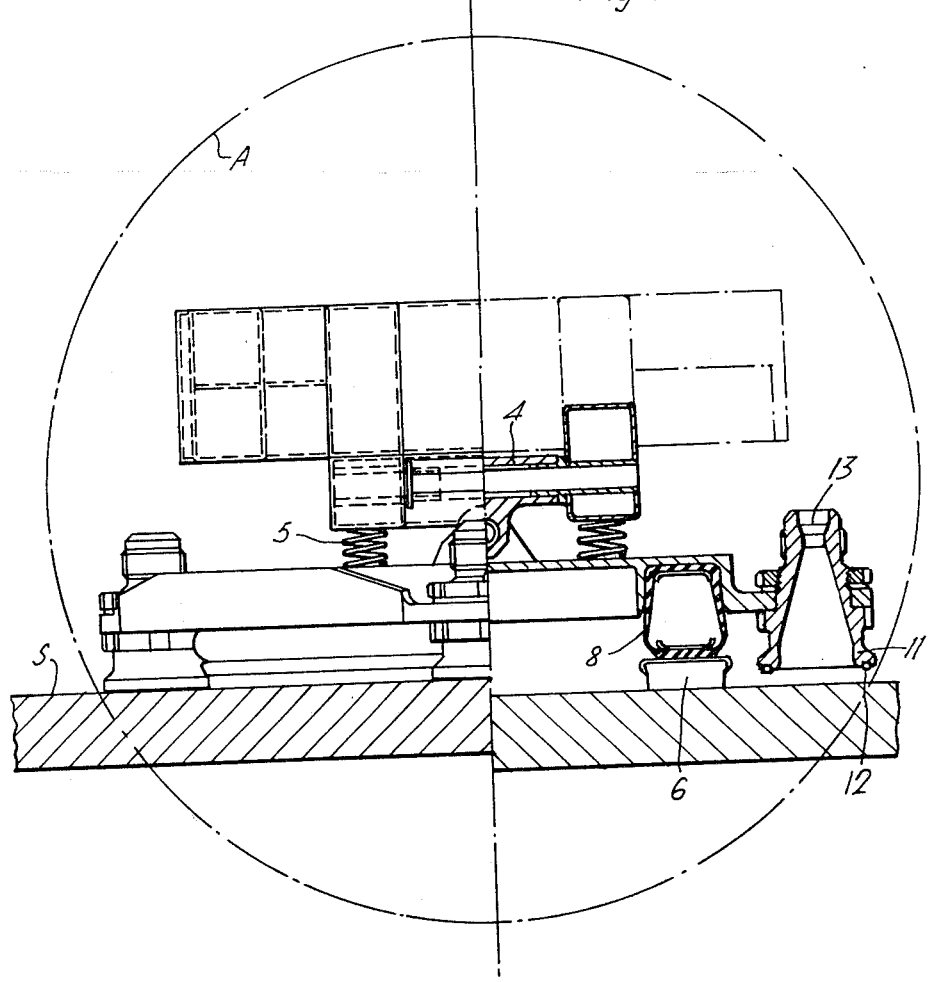

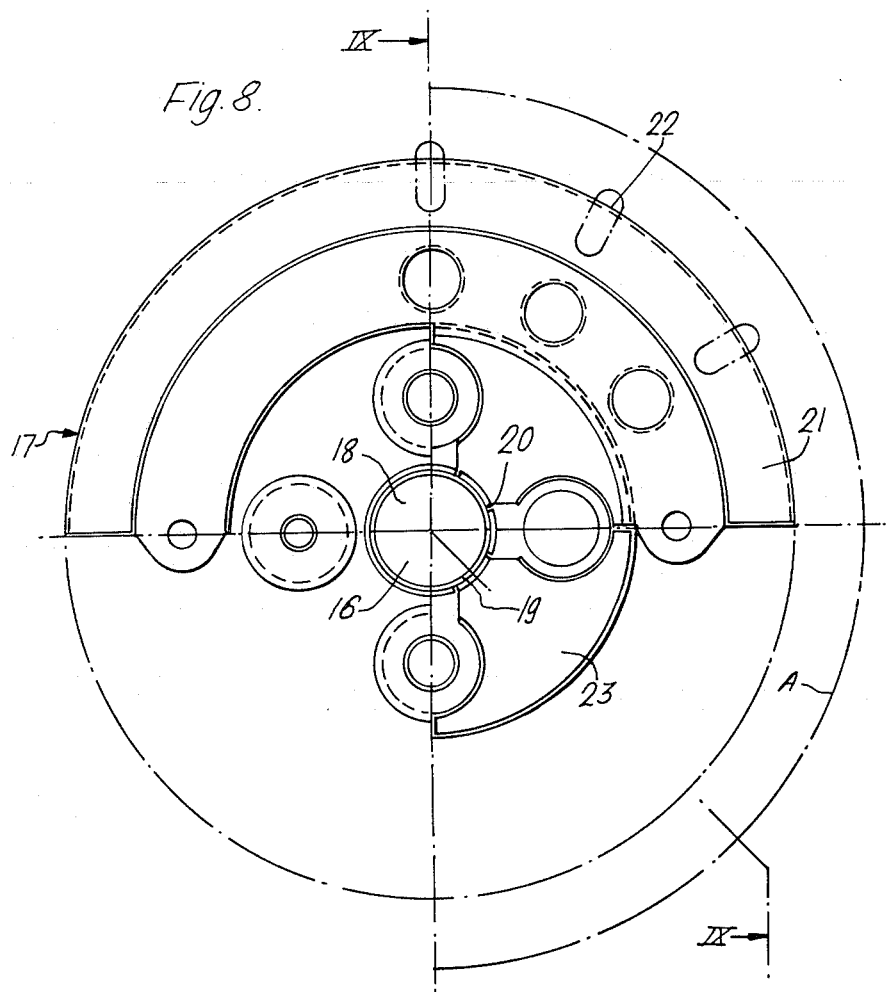

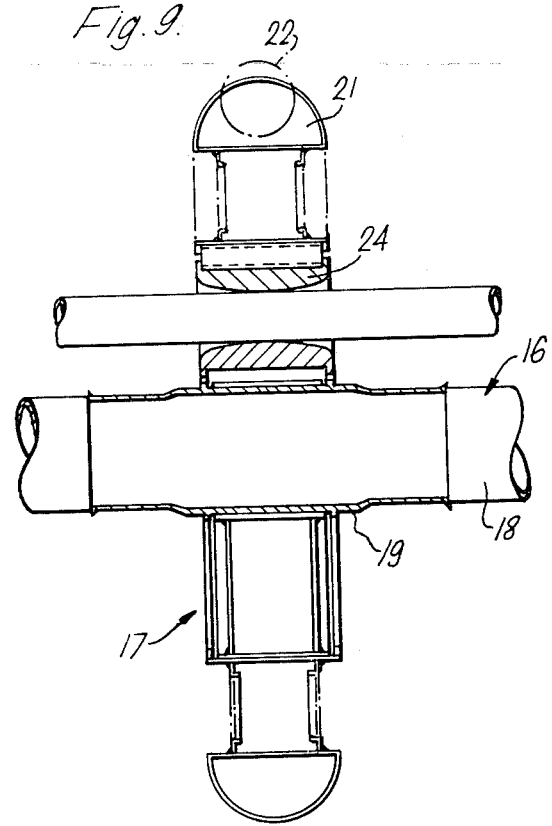

NON-DESTRUCTIVE TEST APPARATUS

BACKGROUND OF THE INVENTION

This invention relates to non destructive test apparatus and provides a free roving vehicle for carrying inspection instrumentation over a remote surface.

A vehicle according to the invention finds application in the inspection of a primary vessel of a construction of liquid metal cooled nuclear reactor of the pool kind. Such a nuclear reactor construction comprises a nuclear fuel assembly submerged in a pool of liquid metal coolant contained in the primary vessel which is housed in a concrete containment vault. In use the primary vessel is subject to irradiation and to severe thermal stress so that periodic inspection of the vessel is required to ensure its continued integrity. Inspection of the primary vessel is difficult because it must be carried out on its external surface by remotely operated apparatus.

SUMMARY OF THE INVENTION

According to the invention a vehicle for carrying non destructive test instrumentation over a remote surface comprises a bridge structure having a plurality of support pads pivotally mounted thereon, each support pad having suction means for adhering the vehicle to an inclined or inverted surface and fluid thrust means arranged in opposition to the suction means to facilitate lateral sliding displacement of the vehicle and a resiliently flexible tubular tie member for suspending the bridge structure and conducting fluid supplies thereto.

According to another aspect of the invention a method of inspecting the primary vessel of a liquid metal cooled nuclear reactor of the pool kind housed in a closed vault comprises mounting inspection instrumentation including a television camera on a vehicle, suspending the vehicle and instrumentation in an interspace bounded by the primary vessel and the vault, adhering the vehicle to the vessel by suction means, vertically displacing the vehicle in step wise manner and intermittently anchoring the vehicle to the surface of the vessel by the suction means prior to inspection of the surrounding terrain.

DESCRIPTION OF THE DRAWINGS

A constructional embodiment of the invention and a method of inspecting the primary vessel of a liquid metal cooled nuclear reactor of the pool kind are described, by way of examples, with reference to the accompanying drawings wherein:

FIG. 5 is an end view in section on line V—V of FIG. 1, FIG. 8 is a part plan view in section on line VIII—VIII of FIG. 6 showing a services support ring, and FIG. 9 is a section on line IX—IX of FIG. 8.

DESCRIPTION OF THE PREFERRED EMBODIMENT

Figure 1:
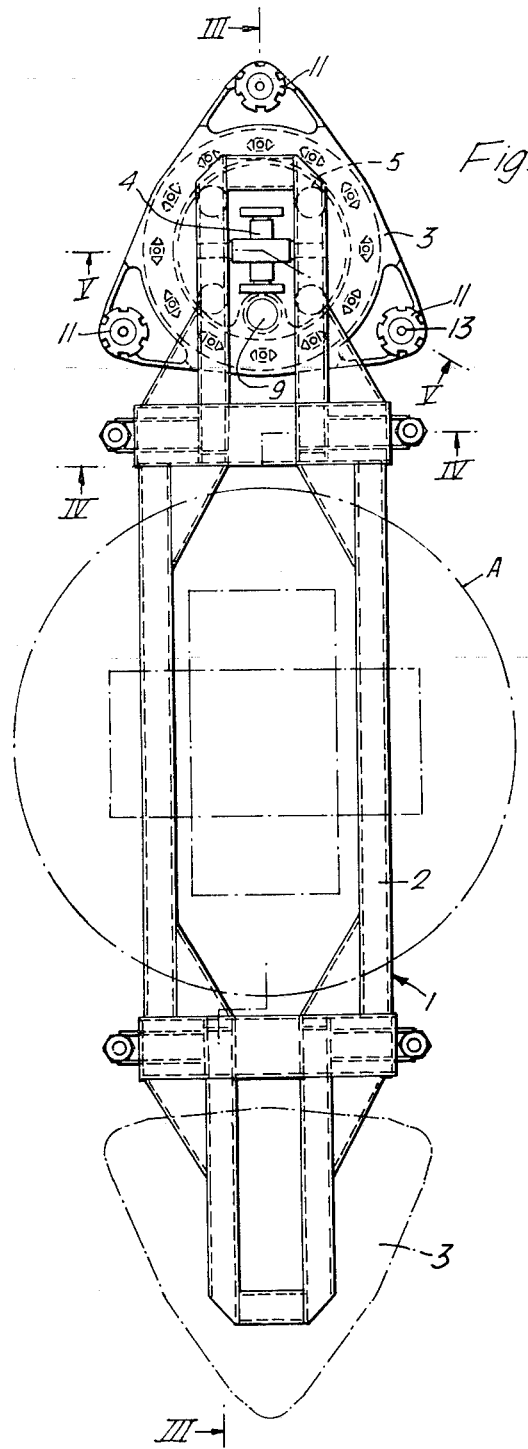
FIG. 1 is a fragmentary plan view of a vehicle for carrying non destructive test instrumentation.
Figure 2:
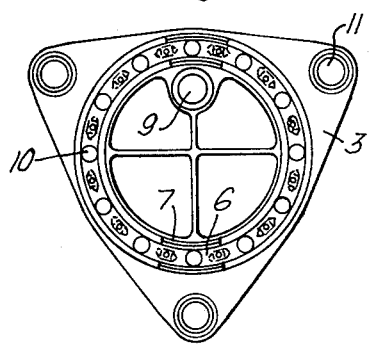
FIG. 2 is an inverted fragmentary plan view.
Figure 3:
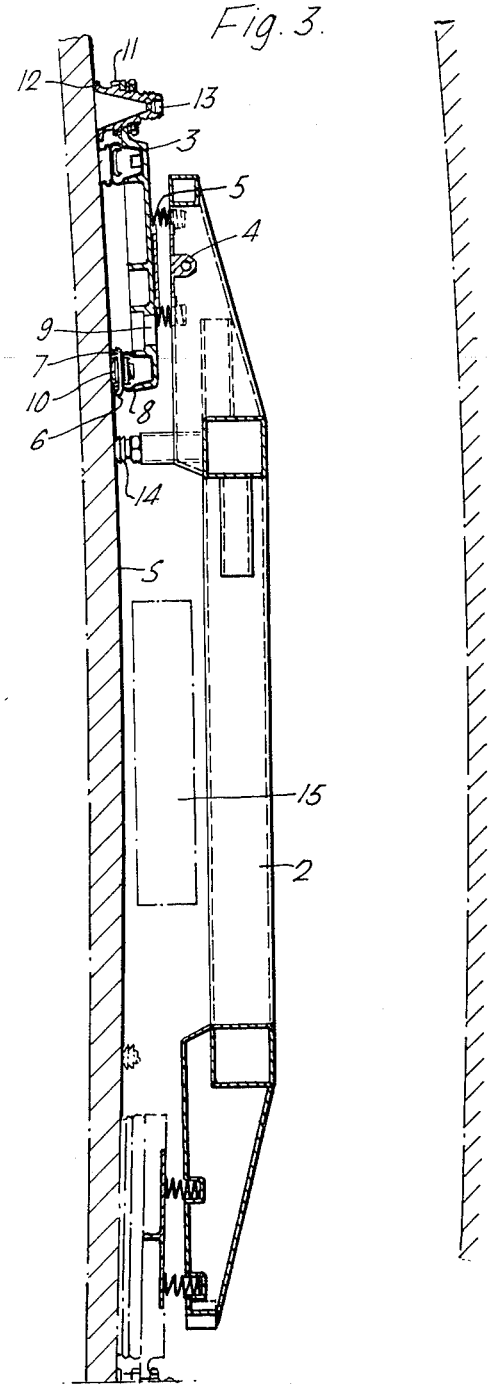
FIG. 3 is a diagrammatic side view in section on line III—III of FIGS. 1 and 2.
Figure 4:
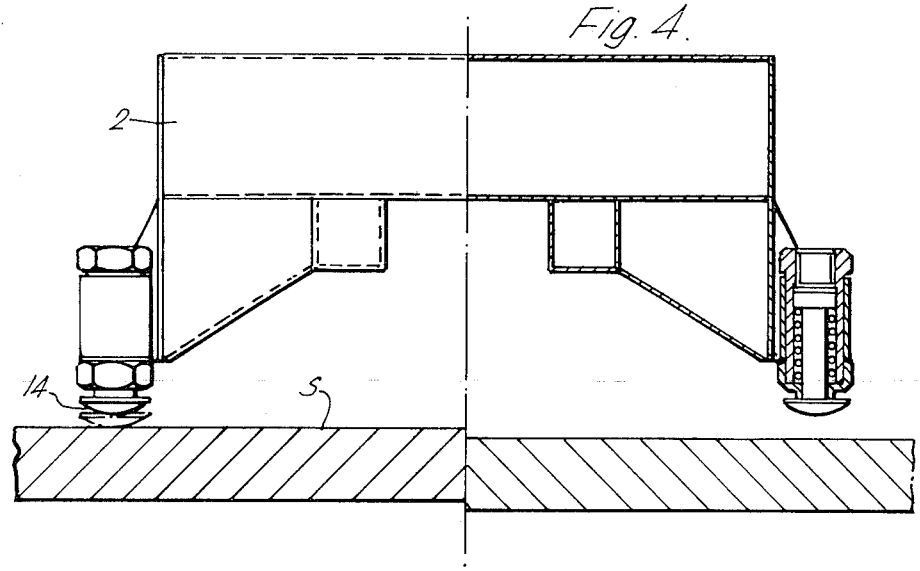
FIG. 4 is an end view in section on line IV—IV of FIG. 1.
Figure 7:
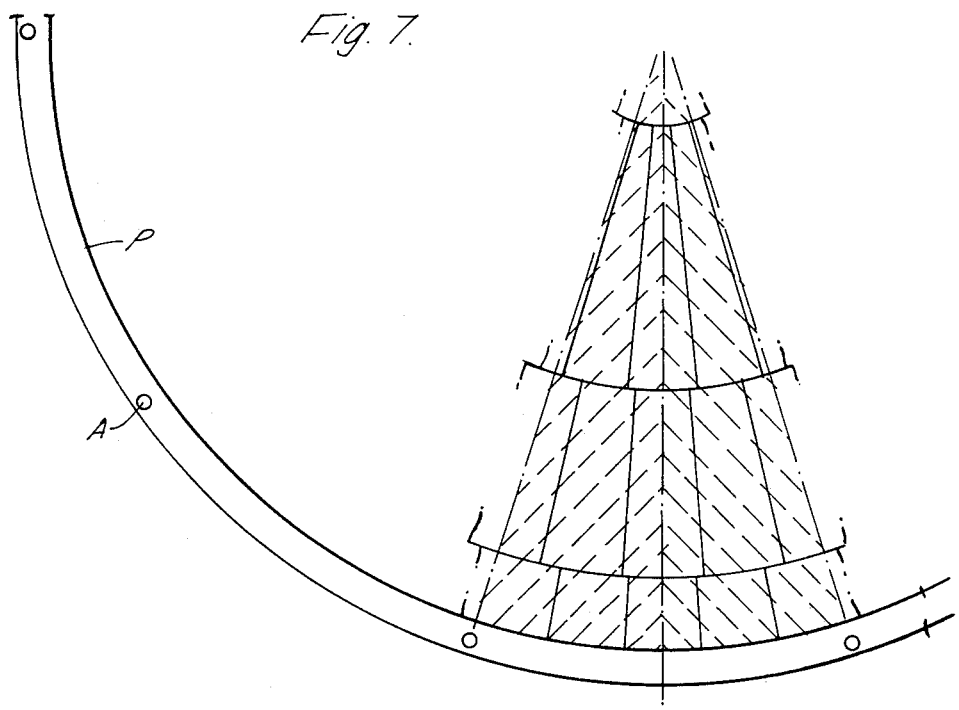
FIG. 7 is a fragmentary plan view of the nuclear reactor construction.

With reference to FIGS. 1 to 5, the vehicle designated 1, for carrying non destructive test instrumentation, is constructed mainly of titanium enabling it to withstand the high temperature of its operational environment and comprises an elongate bridge structure 2 having two support pads 3 carried one at each end on gimbal mountings 4 each with four alignment springs 5 interposed between one support pad 3 and the bridge structure 2. Each support pad 3 has an annular seal member 6 having a series of concentric lips 7 of synthetic rubber providing a labyrinth seal and mounted on a resiliently deformable ring 8. A suction source connection 9 penetrates each pad 3 into a void bounded by the sealing member 6 and an annular series of bearing pads 10 of low friction material comprising polytetrafluoroethylene containing 15% glassfilling is disposed concentrically between the inner and outer annular lips 7. Each support pad 3 also carries three gas thrusters 11 comprising tubular ducts having gas pressure connections 13 and each thruster has a high friction elastomeric ring 12 disposed in its end face. The bridge structure 2 has four jack operated retractable stabilising feet 14 and is adapted at 15 for carrying inspection apparatus (not shown) such as a television camera and an ultrasonic probe unit. The instrumentation is arranged to be rotatable through 90° and to be capable of limited lateral displacement relative to the bridge.

In use to inspect a curved surface designated 'S' in the drawings the vehicle can be anchored to the surface with its longitudinal axis vertical by applying suction to the pads by way of the connections 9. The resiliently deformable rings 8 urge the lips 7 of the labyrinth seals into contact with the surface, the bearing pads 10 serving to limit the deflection of the sealing lips. The gimbal mountings 4 enable the suction pads to pivot universally with the aid of the springs 5 to accommodate curvature of the surface whilst the rings 12 serve to resist sliding of the vehicle when adhering to the wall of the vessel. The stabilising feet 14 can be urged into contact with the surface to stabilise the vehicle during inspection operations. Although not shown in the drawings, the vehicle is provided with laterally disposed reaction propulsion nozzles for laterally displacing the vehicle. To displace the vehicle over the surface, gas pressure is applied to the thrusters 11 so that the friction rings 12 are caused to lift substantially clear of the surface. The resiliently deformable rings 8 extend to ensure that the lips of the labyrinth seal remain in sealing contact with the surface, any tendency for lift-off to increase due to external forces being resisted by increased depression in the void.

For use in inspecting the outer surface of a primary vessel of a construction of liquid metal cooled nuclear reactor of the pool kind the suction source to each pad may be derived from jet pumps of conventional axial tubular kind which engage the connections 9.

Alternatively, the jet pumps may be of the radial inducer kind as disclosed in the co-pending application entitled Suction pads for supporting loads by R. C. Farmer, H. A. Goldsmith and M. J. Proudlove and filed on the same date as the present application.

Figure 6:
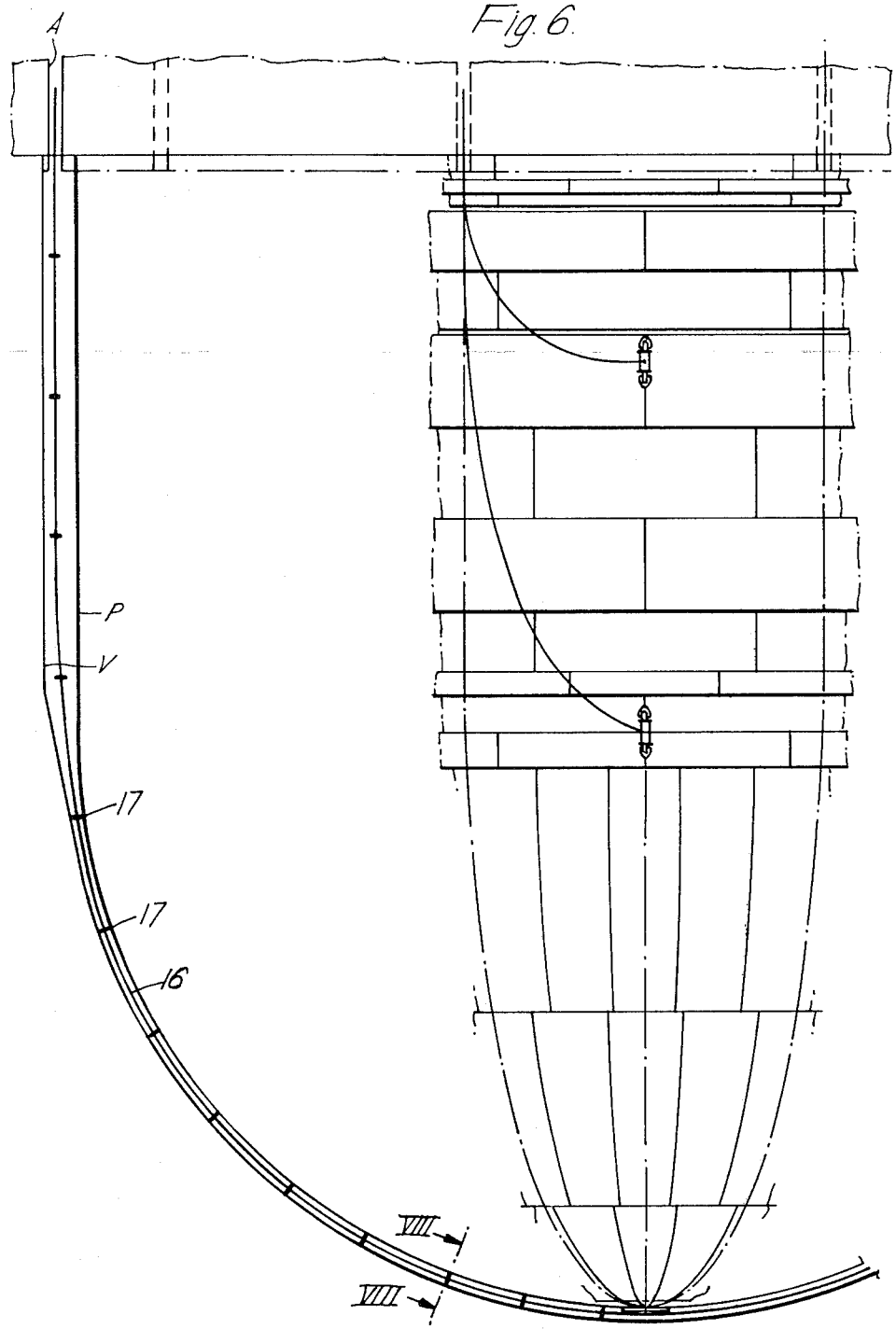
FIG. 6 is a fragmentary side view in section of a nuclear reactor construction.

As shown in FIG. 6, the bridge structure is suspended by a tie member 16 which has plurality of tubular ducts for conducting service fluid to the vehicle. A series of spaced support discs 17 shown in greater detail in FIGS. 8 and 9 is anchored to the tie member 16, the discs serving to support the tie member from adjacent surfaces are spaced at progressively shorter intervals towards the bridge structure. Each support disc 17 shown in FIGS. 8 and 9 is attached to a central hose 18 of the tie member by means of a swaged collar 19 which grips the hose and is radially located in the disc by dogs 20. A split outer ring 21 has twelve equally spaced rollers 22 for bearing on the adjacent surfaces. An inner yoke 23 is divided into four segmented spacers for supporting gas pressure hoses which pass freely through the disc by way of fair-leads 24 so that they can move relative to the central hose and thereby accommodate surface curvature. The radial loction of the disc on the swaged collar prevents twisting of the hoses.

The vehicle is used for carrying television and ultrasonic apparatus for the inspection of a primary vessel designated P in FIG. 6 which is housed in the vault V. The primary vessel is generally cylindrical with a hemispherical base and the cover of the vault has twelve equally spaced access apertures designated A through which the vehicle can be threaded together with its tie member. To inspect the vessel P, the vehicle with inspection instrumentation mounted thereon is passed through a selected aperture A and suspended in the interspace between the vessel and the wall surface of the vault by the tie member 16. The vehicle is anchored to the vessel by the vacuum means whilst the surface of the vessel in the region of the vehicle is scanned. The vehicle is displaced vertically in step wise manner being intermittently anchored for scanning operation.

The vehicle is capable of being anchored in any latitude on each of twelve lines of longitude of the primary vessel and by partial rotation of the television camera and ultrasonic probes the entire surface area of the vessel can be scanned. The strake welds of the primary vessel have identification marks so that the position of the vehicle can be monitored visually by means of the television camera. The support discs bear against the wall surface of the vault and the primary vessel and the progressively reduced pitching of the discs provides adequate support for the tie member in the vicinity of the pole of the hemisphere.

It is envisaged that the vehicle may also be used for inspecting storage tanks or other recepticles where access is limited for any reason.

In an alternative construction (not illustrated) the bridge of the vehicle comprises a triangular frame having a support pad at each corner. The frame is hinged at three axes arranged so that each support pad is capable of swinging about an axis lying parallel to the side which is opposed to the support pad. The alternative construction of vehicle would be capable of negotiating corners in a building or tank construction.

We claim:

1. A vehicle for carrying non-destructive test instrumentation over a remote surface, the vehicle comprising a bridge structure having a plurality of support pads pivotably mounted thereon, each support pad having suction means for adhering the vehicle to an inclined or inverted surface and fluid thrust means arranged in opposition to the suction means to facilitate lateral sliding displacement of the vehicle, and a resiliently flexible tubular tie member for suspending the bridge structure and conducting fluid supplies thereto.

2. A vehicle according to claim 1 wherein each support pad has an extensible face seal for bounding an evacuable void between the pad and the surface, the suction means being arranged to evacuate the void, and the fluid thrust means being operable selectively to lift the pad by extending the seal against vacuum.

3. A vehicle according to claim 2 wherein the extensible face seal of each support pad comprises an annular resiliently deformable member secured to the pad and surmounted by an annular seal member having a series of concentric annular lips disposed for making sealing abutment with the surface.

4. A vehicle according to claim 3 wherein each support pad has an annular series of bearing pads disposed concentrically between the inner and outer lips of the seal member.

5. A vehicle according to claim 4 wherein the fluid thrust means comprises a plurality of tubular gas ducts each carrying elastomeric members disposed for anti sliding abutment with the surface when the pad adheres.

6. A vehicle according to claim 1 wherein the vehicle has retractable stabilising feet for abutment with the surface.

7. A vehicle according to claim 6 wherein the tie member carries a series of co-axial disposed spaced discs for supporting and guiding the tie member within an annular void, the discs having an annular series of rollers for bearing on surfaces bounding the annular void.

8. A vehicle according to claim 7 provided with a plurality of reaction propulsion nozzles for laterally displacing the vehicle.

* * * * *